(12) United States Patent
Stutzenberger et al.

(10) Patent No.: US 7,682,631 B2
(45) Date of Patent: Mar. 23, 2010

(54) ADHESIN-SPECIFIC NANOPARTICLES AND PROCESS FOR USING SAME

(75) Inventors: Fred J. Stutzenberger, Clemson, SC (US); Robert A. Latour, Jr., Clemson, SC (US); Ya-Ping Sun, Clemson, SC (US); Tzuen R. Tzeng, Central, SC (US)

(73) Assignee: Clemson University, Clemson, SC (US)

( * ) Notice: Subject to any disclaimer, the term of this patent is extended or adjusted under 35 U.S.C. 154(b) by 1903 days.

(21) Appl. No.: 10/677,132

(22) Filed: Oct. 1, 2003

(65) Prior Publication Data

US 2007/0184120 A1 Aug. 9, 2007

(51) Int. Cl.
A61K 9/14 (2006.01)
A61K 38/00 (2006.01)
A61K 51/00 (2006.01)
(52) U.S. Cl. .................. 424/489; 514/2; 424/1.69
(58) Field of Classification Search .................. None
See application file for complete search history.

(56) References Cited

U.S. PATENT DOCUMENTS

| | | | |
|---|---|---|---|
| 5,416,075 A * | 5/1995 | Carson et al. .......... 514/23 |
| 5,484,773 A | 1/1996 | Heerze et al. |
| 5,635,606 A | 6/1997 | Heerze et al. |
| 5,798,260 A | 8/1998 | Tarr et al. |
| 6,013,635 A | 1/2000 | Heerze et al. |
| 6,040,421 A | 3/2000 | Tarr et al. |
| 6,107,282 A | 8/2000 | Heerze et al. |
| 6,270,755 B1 | 8/2001 | Bacon Kurtz et al. |
| 6,291,435 B1 | 9/2001 | Yanmaele et al. |
| 6,355,276 B1 | 3/2002 | Illum et al. |
| 6,358,930 B1 | 3/2002 | Heerze et al. |
| 6,387,408 B1 | 5/2002 | Illum et al. |
| 6,465,435 B1 | 10/2002 | Heerze et al. |
| 6,750,016 B2 | 6/2004 | Mirkin et al. |
| 6,890,523 B2 | 5/2005 | Bacon Kurtz et al. |
| 2003/0147966 A1* | 8/2003 | Franzen et al. ............ 424/491 |
| 2003/0223938 A1 | 12/2003 | Nagy et al. |

OTHER PUBLICATIONS

Article—*Selective Binding of Mannose-Encapsulated Gold Nanoparticles to Type 1 Pili in Escherichia coli*, Chun-Cheng Lin, Yi-Chun Yeh, Chan-Yi Yang, Chan-Long Chen, Gee-Fong Chen, Chia-Chun Chen, and Yi-Chun Wu, J. Am. Chem. Soc., vol. 124, No. 14, 2002, pp. 3508-3509.

Article—*Adhesion, Bacterial*, Matthew A. Mulvey and Scott J. Hultgren, Encyclopedia of Microbiology, vol. 1, 2000, pp. 42-47.

Article—*Enteric Immunization: Promises and Challenges*, William R. Brown, Digestive Diseases, vol. 14, 1996, pp. 192-200.

Article—*Syntheses and Properties of Novel Vinyl Monomers Bearing a Glycoside Residue*, Sadaya Kitazawa, Masakazu Okumura, Keisuke Kinomura, and Toshiyuki Sakakibara, The Chemical Society of Japan, Chemistry Letters, 1990, pp. 1733-1736.

Article—*Unusual Size Formation of Polymeric Nanospheres Synthesized by Free Radical Polymerization in Ethanol-Water Mixed Solvents*, Takeshi Serizawa, Ming-Qing Chen, and Mitsuru Akashi, Langmuir, vol. 14, No. 5, 1998, pp. 1278-1280.

Article—*Preparation and applications of polyethylene glycol-polystyrene graft resin supports for solid-phase peptide synthesis*, Samuel Zalipsky, Jane L. Chang, Fernando Albericio, and George Barany, Reactive Polymers, vol. 22, 1994, pp. 243-258.

Article—*Use of a Fluorescent Redox Probe for Direct Visualization of Actively Respiring Bacteria*, G. G. Rodriguez, D. Phipps, K. Ishiguro, and H. F. Ridgeway, Applied and Environmental Microbiology, vol. 58, No. 6, Jun. 1992, pp. 1801-1808.

Article—*Polymers with Pendent Saccharides—'Glycopolymers'*, Takashi Miyata and Katsuhiko Nakamae, TRIP, vol. 5, No. 6, Jun. 1997, pp. 198-206.

Information—*Entamoeba histolytica*, 3 pages, www.biosci.ohio-state.edu, Aug. 15, 2003.

Information—*Entamoeba histolytica* Whole Genome Shotgun, 1 page, www.sanger.ac.uk, Aug. 15, 2003.

(Continued)

*Primary Examiner*—Maury Audet
(74) *Attorney, Agent, or Firm*—Dority & Manning, P.A.

(57) ABSTRACT

The present invention is generally directed to compositions useful in preventing and/or treating disease due to infection by any of a variety of biologically active pathogenic microorganisms. The compositions include nanoparticles formed of a hydrophobic polymeric core, hydrophilic linking agents bound to the core, and biofunctional materials bound to the linking agents. The biofunctional materials are functionally identical to receptors on host cell surfaces that can be recognized and bound by adhesins on the surface of the targeted pathogenic adhesin-bearing microorganisms. In one embodiment, the binding action between the nanoparticles and the microorganisms can lead to the formation of large agglomerated complexes, which can then be easily removed from an area, including the digestive tract of an infected individual. The compositions of the present invention can also be utilized in preventing enteric infections via the ability to purge animals of enteropathogens prior to transport and processing for human consumption.

9 Claims, 8 Drawing Sheets

OTHER PUBLICATIONS

Information—Bacteria: Life History and Ecology, 2 pages, www.ucmp.berkeley.edu, Aug. 18, 2003.
Information—*Campylobacter jejuni*, 4 pages, www.cfsan.fda.gov, Aug. 15, 2003.
PCT Search Report and Written Opinion for PCT/US04/30090, May 27, 2005.
Garcia, et al. "Campylobacters important in veterinary medicine", Vet. Bulletin 53: 793-818 (1983).
Friedman, et al., "Epidemiology of *Campylobacter jejuni* in the United States and other industrialized countries", In: *Campylobacter*, $2^{nd}$ ed., p. 121-138, ASM Press, Washington, DC (2000).
Abstract—Tauxe, R.V., et al., "Epidemiology of *Campylobacter jejuni* infections in the United States and other industrialized nations", p. 9-19, In: *Campylobacter jejuni*. Current Status and Future Trends American Society for Microbiology, Washington, DC (1992).
Robinson, D.A., "Infective dose of *Campylobacter jejuni* in mild", Br. Med, J. 282: 1584 (1981).
Taylor, et al., "Influence of strain characteristics and immunity on the epidemiology of *Campylobacter* infections in Thailand", J. Clin. Microbiol. 26:863-868 (1988).
Abstract—Franco, D.A., "*Campylobacter* species: considerations for controlling a food-borne pathogen", Food Prot. 51:145-153 (1988).
Shane, S. M., "Environmental factors associated with *Campylobacter jejuni* colonization of poultry", p. 29-46, In: Colonization Control of Human Bacterial Enteropathogens in Poultry, Academic Press, San Diego (1991).
Abstract—Shih, "Isolation and identification of enteropathogenic *Campylobacter* spp. From chicken samples in Taipei" J. Food Prot. 63:304-308 (2000).
Kazwala, et al., The establishment and spread of *Campylobacter jejuni* in young chickens: experimental studies p. 118-121 In: Prevention and Control of Potentially Pathogenic Microorganisms in Poultry and Poultry Processing, Het Spelderholt, Ploufragan, France (1990).
Abstract—Pearson, et al., "Continuous source outbreak of campylobacteriosis traced to chickens" J. Food Prot. 63:309-314 (2000).
Shanker, et al. "Horizontal transmission of *Campylobavter jejuni* amongst broiler chicks: experimental studies", Epidemiol. Infect. 104:101-110 (1990).
Abstract—Stern, et al., "Colonization characteristics of *Campylobacter jejuni* in chick ceca." Avian Dis. 32:220-334 (1988).
Montrose, et al., Role of litter in the transmission of *Campylobacter jejuni* Avian Dis. 29:392-399 (1985).
Abstract—Stern, et al., "*Campylobacter* spp. In broilers on the farm and after transport" Poultry Sci. 7:937-941 (1995).
Deming, et al., "*Campylobacter enteritis* at a university: transmission from eating chicken and from cats" Amer. J. Epidemiol. 126:526-534. (1987).
Abstract—Norcross, et al., Importance of *Campylobacter* spp. To the food industry. In: *Campylobacter jejuni*. Current Status and Future Trends p. 61-65 (1992).
Fairchild, et al., "Disk diffusion antimicrobial susceptibility tests against avian *Escherichia coli* isolates", Poultry Sci. 77 (Supp. 1): 94 (1998).
Fairchild, et al., "Effect of hen age, Bio-Mos and Flavomycin on susceptibility of turkey poults to oral *Escherichia coli* challenge. In: Under the Microscope: Focal Points for the New Millenium", Biotechnology in the Feed Industry, Proceedings of Alltech's $15^{th}$ Annual Symposium, Nottingham University press, Nottingham, UK, pp. 185-201 (1999).
Sun, et al., "Preparation and Characterization of Highly Water-Soluble Pendant Fullerene Polymers", Macromolecules, 32, 8747 (1999).
An, et al., *Handbook of Bacterial Adhesion, Principles, Methods and Applications* Humana Press, (2000).
Abstract—Vogt, et al., Campylobacter enteritis associated with contaminated water, Ann. Intern. Med. 96:292-296 (1982).

* cited by examiner

ADHESIN-SPECIFIC NANOPARTICLES AND PROCESS FOR USING SAME

BACKGROUND OF THE INVENTION

The biological sources of infection to humans are wide and varied. For instance, bacteria in the genera *Campylobacter, Listeria, Salmonella, Shigell* and *Vibrio*, as well as various protozoa such as *Giardia intestinalis*, and *Entamoeba histolytica* have long been known to cause enteric infections. More recently, bacteria in the genera *Aeromonas, Escherichia* and *Helicobacter* as well as rotaviruses and Norwalk-like viruses have been identified as causative agents of enteric infections. Recently, concern has been raised that biological pathogens, including viruses and spores, may be utilized by bioterrorists to cause widespread infection through introduction into food, water, or air.

Enteropathogens are spread via contaminated food or water, and are some of the most virulent and easily communicated pathogens. Symptoms of enteropathogenic infections can range in severity from mild transient diarrhea, cramping and nausea to life-threatening dehydration, toxemia and circulatory collapse. Improved food sanitation, municipal water purification and personal hygiene have greatly reduced the incidence of enteric infection in the developed world. These diseases still pose a dangerous threat, however, especially in the developing world, particularly for children, as infection often leads not only to disease, but often to death.

Attempts have been made to develop antibiotics and vaccinations against some of the pathogens that cause enteric infections, but these attempts have met with limited success. Such agents tend to be quite expensive, both in development and production costs. In addition, the sheer variety of pathogenic microorganisms, combined with the ability of the pathogens to quickly develop resistance to antibiotics and vaccines, makes the prospect of developing long lasting, inexpensive preventatives and/or treatments for these diseases by such methods dim. Added to these problems, even in those instances when the immunity gained from an inoculation is accurate for the actual pathogen encountered by the individual, the mucosal immunity gained is short lived (only six months in the case of the cholera vaccine).

As such, what is needed in the art is a method of preventing such infections before they begin. What are needed in the art are products and methods that can prevent the initial attack of a host by a biological pathogen. In addition, what are needed in the art are products that can be utilized to label pathogens in, for example, identification procedures.

SUMMARY OF THE INVENTION

In one embodiment, the present invention is directed to a nanoparticle that includes a hydrophobic polymeric core, a hydrophilic linking agent bound to the polymeric core, and a biofunctional material that is capable of binding to a biologically active microorganism bound to the linking agent. For instance, the biofunctional material bound to the nanoparticle can include a binding site for adhesins present on the surface of a targeted microorganism.

In another embodiment, the present invention is directed to a composition comprising the nanoparticle. In one embodiment, the composition can include an aqueous suspension of the nanoparticles.

The nanoparticles of the invention can be formed in a variety of sizes and can include many different core, linking, and biofunctional materials. For example, the nanoparticles can have an average diameter between about 30 nm and about 5 μm. In one embodiment, the nanoparticles can have an average diameter between about 50 nm and about 1 μm.

The hydrophobic polymeric core can be, for example, a styrene polymer or a methyl methacrylate polymer. In one embodiment, the hydrophobic polymeric core can be a crosslinked polystyrene core.

Exemplary hydrophilic linking agents can include polyethylene glycol and polypeptides. In certain embodiments of the invention, the linking agents may be derivatized, for example to bind to both the core material and the biofunctional material as desired. The linking agent can generally extend off of the surface of the core for a distance. For instance, the linking agent can have a degree of polymerization between about 10 and about 200. In one embodiment, the linking agent can have a degree of polymerization between about 20 and about 100.

The biofunctional material can include glycolipids, glycoproteins, peptides, polypeptides, lipids, monosaccharides, polysaccharides, and derivatives thereof. In one embodiment, the biofunctional material can be a simple carbohydrate moiety, such as mannose or mannan, for example. Optionally, the nanoparticles can include more than one type of biofunctional material on the surface.

The nanoparticles can be specifically designed to target a biologically active microorganism such as, for example, pathogenic bacterial, eucaryotic, and/or viral microorganisms. In one embodiment, the composition can target specific enteropathogenic microorganisms such as *C. jejuni* or *E. coli*.

The nanoparticles of the invention can optionally carry additional materials, such as antigenic epitopes to be used in immunization or labeling agents, for delivery to the targeted microorganisms.

The nanoparticles can be formed by any suitable polymerization method, and may be formed utilizing either a converging or a diverging polymerization approach. In a diverging approach to polymerization, a macromolecule can be formed including the linking agent and a monomer of the core material. The macromolecule can then be polymerized with monomers of the core material to form a non-biofunctionalized nanoparticle. Finally, the biofunctional material can be bound to the surface of the nanoparticle following polymerization. In a converging approach, the macromolecule can include a monomer of the core material, the linking agent, and the biofunctional material. The macromolecule thus obtained can then be polymerized with monomers of the core material and the biofunctionalized nanoparticles can be formed in a single polymerization step.

The compositions of the present invention can be utilized to agglomerate targeted microorganisms. The large, agglomerated complexes formed of nanoparticles bound to multiple microorganisms can be removed from an area and the composition can thus be utilized to decontaminate an area. In one embodiment, the agglomerated complexes can be formed within the digestive tract of an animal after the biofunctional nanoparticles that are biofunctionalized to compete with the native host cell receptors for the microbial adhesin sites have been ingested. In this embodiment, the formation of the agglomerated complexes can be used to purge the animal of the microorganisms. For example, the large agglomerated complexes can be removed from the digestive tract via the natural peristaltic action of the animal. For instance, animals can be purged of pathogenic microorganisms prior to transport and processing. In one particular embodiment, chickens can be purged of *C. jejuni* prior to transport. In another particular embodiment, cattle can be purged of *E. coli* prior to being sent to a slaughterhouse. This can help to prevent the spread of enteric pathogens from an infected group of animals to later groups of animals processed on the same equipment as well as help to prevent diseases due to pathogen infection of consumers.

The compositions of the present invention can also be utilized to label targeted microorganisms. For instance, the nanoparticles can include a label, such as a fluorescent label, which can then be detected following the binding of the nanoparticles to the targeted microorganisms.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying figures, in which.

Figure 1:
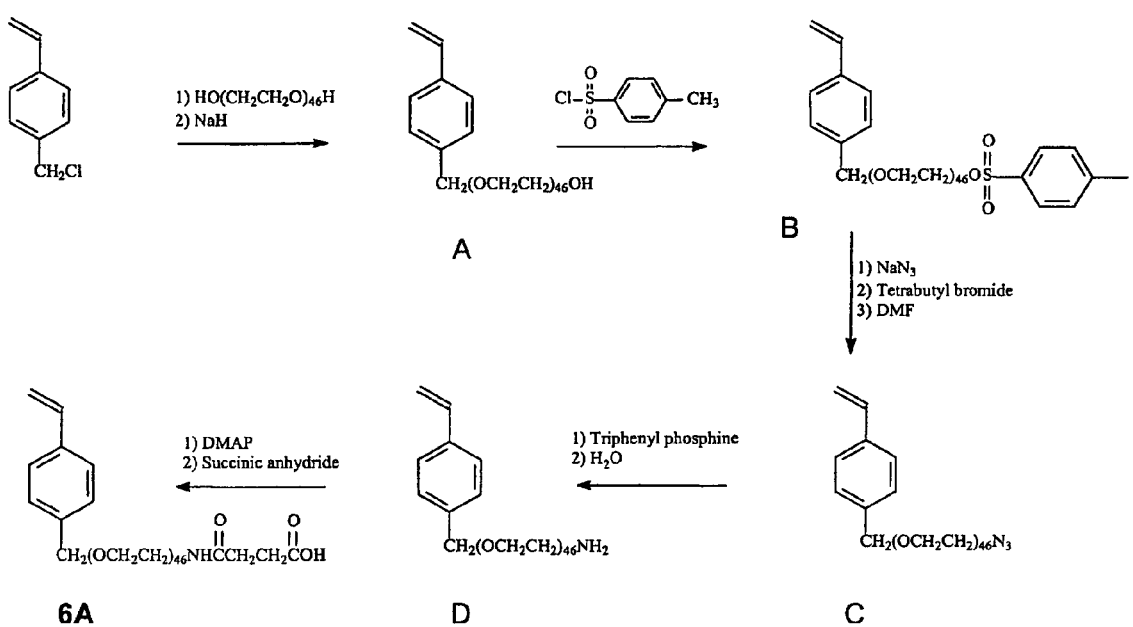
FIG. 1 is a formation mechanism for a carboxylic acid terminated-styrene-polyethylene glycol (PEG) macromonomer that can be utilized in forming biofunctionalized nanoparticles of the present invention.

Repeat use of reference characters in the present specification and drawings is intended to represent the same or analogous features or elements of the present invention.

DETAILED DESCRIPTION OF THE INVENTION

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment. Thus, it is intended that the present invention should cover such modifications and variations as come within the scope of the appended claims and their equivalents.

The present invention is generally directed to materials and compositions useful in preventing and/or treating disease due to infection by any of a variety of biologically active pathogenic microorganisms. More specifically, the compositions of the present invention include a component that can securely bind to a targeted biologically active microorganism, such as a pathogenic microorganism.

The invention is also directed to methods for utilizing the disclosed materials. For example, the disclosed materials can be utilized for prevention and/or treatment of infections caused by pathogenic microorganisms. The materials can also be utilized for identifying biological microorganisms or for decontaminating areas that may contain pathogenic microorganisms. Moreover, the disclosed materials can be very safe and non-toxic to hosts. As such, the materials may be safely used with humans or animals.

The compositions of the present invention include biofunctionalized nanoparticles that can bind to targeted microorganisms. The biofunctionalized nanoparticles include a hydrophobic polymeric core, hydrophilic linking agents attached to the polymeric core, and biofunctional moieties attached to the linking components. The biofunctional moieties can be functionally identical to host cell receptors that can be recognized and bound by the targeted microorganisms in nature. As such, when the compositions of the present invention are in the vicinity of the targeted microorganisms, the microorganism will bind to the biofunctional moiety of the nanoparticle. In one embodiment, this binding can prevent initial infection of a host by the microorganism. In another embodiment, this binding can occur after initial attack of a pathogenic microorganism, but can lead to the detachment of the pathogen from the cell of an already infected host or the inactivation of the pathogenic agent.

In another embodiment, the compositions of the present invention can be utilized to decontaminate or purge an area of biologically active microorganisms via formation of agglomerated complexes of one or more nanoparticles bound to multiple pathogens. The agglomerated complexes can be easily collected or removed from a contaminated area. The nanoparticles of the present invention can also be labeled and used to tag or otherwise identify targeted biological materials.

In general, the nanoparticles of the present invention can target and bind to any biologically active microorganism that initiates attachment to a host via an attaching/effacing (A/E) mechanism. Microorganisms have evolved a number of mechanisms to facilitate the A/E mechanism of attachment. For purposes of this disclosure, the A/E mechanism is defined as the utilization by the microorganism of one or more surface adhesins to recognize and bind with receptors that are either on the surface of a host cell or a component of the extracellular matrix (ECM). Adhesins are usually proteins or polypeptides located on the surface of microorganisms that can display various specificities for a wide range of host cell receptor molecules. Adhesins can be present on pathogens as components of filamentous, nonflagellar structures, known as pili or fimbriae, or alternatively as afimbrial monomeric or multimeric proteins anchored within the surface membrane of the microorganism. Adhesins need not be proteins or polypeptides, however. Other nonprotein components of membranes, including lipopolysaccharides (LPS), and lipteichoic acid, for example, can function as adhesins as well. Biologically active microorganisms that utilize the A/E mechanism and can be targeted by the nanoparticles of the present invention can include prokaryotic microorganisms and eucaryotic microorganisms as well as viruses and spores.

The nanoparticles of the present invention have at their center a polymeric, hydrophobic core. Polymeric materials are generally preferred for the cores of the nanoparticles as they can allow for wide variation in size of the nanoparticles, which can desirably vary depending upon the application. In addition, polymeric materials can be used to form the core relatively inexpensively when compared to other materials utilized for drug delivery mechanisms in the past (e.g. gold). They can also be quite safe to use, and will not exhibit toxicity found with other materials, such as heavy metals.

In one embodiment, the core can be polystyrene. Other materials may also be utilized as the polymeric core material, however. For example, in one embodiment, the polymeric core may be a polymethyl methacrylate material. Copolymers of styrene and methyl methacrylate may also form the hydrophobic polymeric core. Other materials that can be utilized as the core material can include polymers or copolymers of methyl acrylate, vinyl acetate, (α-methylstyrene, lactic acid, and the like. In one embodiment, the core can be formed of biodegradable polymers.

Generally, between about 50% and about 80% of the weight of the nanostructure can be the core material with the remainder of the weight split between the linking agents, the biofunctional materials, and any other material that can be part of the nanoparticle. Variations will obviously occur depending upon chain length and make-up of the macromonomer forming the core as well as depending upon the make-up of the other materials.

Bound to the surface of the polymeric core of the nanoparticles are hydrophilic linking agents. In one particular embodiment, the linking agents can be covalently bound to the surface of the polymeric core. The linking agents of the nanoparticles can generally serve two purposes, they can provide a level of hydrophilicity to the nanoparticles and encourage the nanoparticles to remain in suspension in an aqueous environment, and they can tether a biofunctional moiety to the exterior surface of the nanoparticles. To provide the desired amount of hydrophilicity to the nanostructures, the relative amount of the hydrophilic linking agent material, while it can be a very high percentage of the weight of the nanoparticle, if desired, can be quite small. For example, the relative amount of the hydrophilic linking agent material can be less than about 5% of the weight of the nanoparticle, and can provide a suitable level of hydrophilicity to the nanoparticles. In one embodiment, the relative amount of the hydrophilic linking agent need be only from about 3% to about 5% of the molecular mass of the nanoparticle to provide enough hydrophilicity to the nanoparticle.

The linking agents generally extend off of the surface of the core for a distance so as to allow better access to the target microorganisms by the biofunctional materials that are bound to the nanostructures via the linking agents. For example, the linking agents can, in one embodiment, comprise a polymer having a degree of polymerization between about 10 and about 200. In one embodiment, the linking agent can have a degree of polymerization between about 20 and 100, in one embodiment between about 25 and 40, for example between about 29 and about 36.

Suitable inking agents can include hydrophilic polymeric materials that can be bound to both the core material and one or more biofunctional moieties. In certain embodiments, the linking agent can be derivatized in order to promote the formation of the bonds, e.g. covalent bonds. In one embodiment, the linking agent can be a diol or a glycol. For example, in one embodiment, the linking agent can by polyethylene glycol or a derivative thereof. Other materials that can be utilized as the linking agent, either alone or in combination with each other, can include peptides, polypeptides, oligosaccharides, polysaccharides, polyacrylic acid, polyacrylamides, and the like.

The outer surface of the nanoparticles of the present invention includes one or more biofunctional moieties bound to the linking agents. The biofunctional moieties of the present invention can be functionally identical to receptors recognized and bound by the targeted microorganisms, as will be further discussed herein. In general, however, the biofunctional moieties of the present invention can include glycolipids, glycoproteins, polypeptides, lipids, monosaccharides, polysaccharides, and derivatives of any of the above.

Various methods can be utilized to synthesize the nanoparticles of the present invention, depending primarily on the individual constituents of the nanoparticles. In one particular embodiment, the linking agents can be covalently attached to both the polymeric core material as well as to the biofunctional material. The covalent attachments of this embodiment can prevent the desorption of the biofunctional material and allow the active sites of the nanoparticles to be more accessible to the targeted microorganisms. In addition, the formation of covalent attachments between the different sections of the nanoparticles can result in materials that can remain stable essentially indefinitely.

In general, an emulsion polymerization or a dispersion polymerization method can be used to form the nanoparticles. An emulsion polymerization is herein defined as a polymerization reaction whereby monomer(s), initiator, dispersion medium (and possibly colloid stabilizer) are mixed forming initially an inhomogeneous system conducive to the polymerization of the monomer(s) resulting in particles of colloidal dimensions. A dispersion polymerization is herein defined as a precipitation polymerization in which monomer(s), initiator (s), and colloid stabilizer(s) are mixed in a solvent forming initially a homogeneous system conducive to the polymerization of the monomer(s) and producing polymer that is insoluble in the solvent, resulting in formation of polymer particles.

Other suitable polymerization method may alternatively be used in forming the nanoparticles of the present invention, however. For example, microemulsion polymerization, precipitation polymerization, precipitation polycondensation, precipitation polyaddition, or suspension polymerization methods may be used as are generally known in the art.

In general, the biofunctionalized nanoparticles of the present invention can be formed through either a converging or a diverging polymerization approach. For instance, in those embodiments in which the biofunctional moiety to be attached to the surface of the nanoparticle is not susceptible to damage under the conditions of polymerization, a converging approach may be preferred. For example, in those embodiments wherein a carbohydrate moiety such as a monosaccharide, a polysaccharide, or a derivative thereof is the biofunctional material, a converging polymerization process can be utilized. In other embodiments, such as when the biofunctional moieties may be sensitive to the polymerization conditions, a divergent polymerization process may be preferred.

No matter which formation process is utilized, the formed polymeric core can be a very stable material that can remain stable essentially indefinitely. In some embodiments, following polymerization of the core material, the core can be cured or crosslinked to stabilize the nanoparticle. For example, the core can be crosslinked with a divinyl compound such as, for example, divinyl benzene, ethylene glycol dimethacrylate (EGDMA), or 1,6-hexanedio diacrylate (HDODA).

Figure 2:
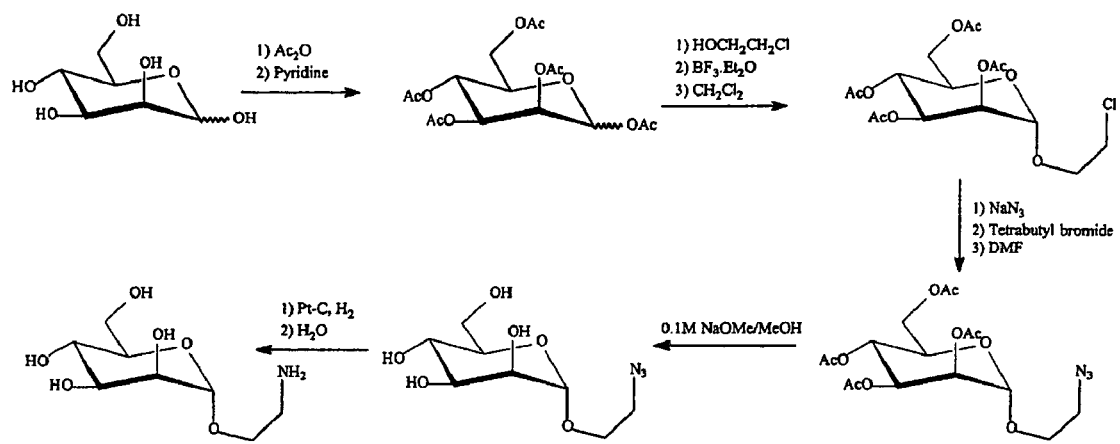
FIG. 2 illustrates a formation mechanism for 2-aminoethyl-α-D-pyranmannoside.
Figure 3:
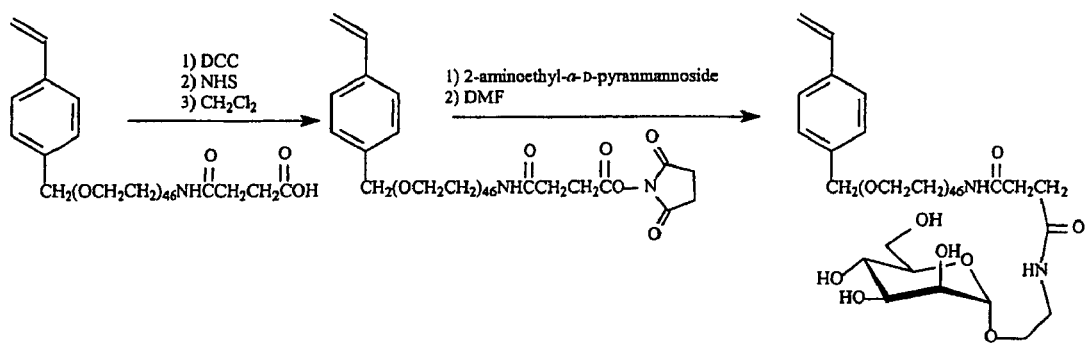
FIG. 3 illustrates a formation mechanism for D-Mannose-containing styrene-PEG macromonomer as may be used in forming mannose biofunctionalized nanoparticles of the present invention.
Figure 4:
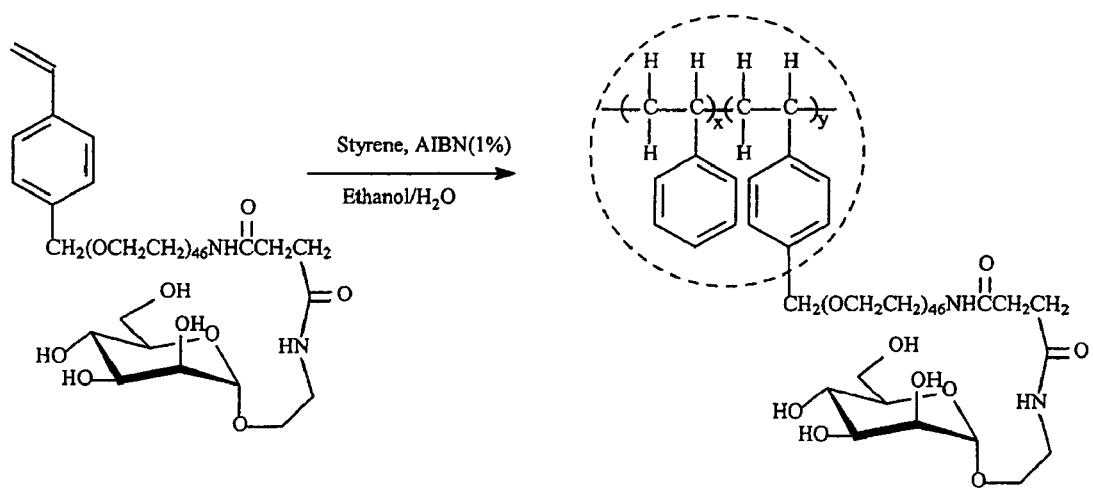
FIG. 4 illustrates a convergent method for forming biofunctionalized nanoparticles including a polystyrene core, a PEG linking agent, and a mannose biofunctional component.

In general, a converging polymerization process is one in which a macromonomer is first formed including the biofunctional moiety, the linking agent, and a monomer of the core material. The macromonomer is then polymerized with other monomers of the core material to form the biofunctionalized nanoparticles of the present invention. For example, in one embodiment, the nanoparticles of the present invention can include a polystyrene core, a polyethylene glycol linking agent, and a monosaccharide such as, for example, a D-mannose biofunctional moiety. In one particular embodiment, this nanoparticle can be formed according to the following converging approach:

1) Preparation of ω-Carboxylic acid-styrene-polyethylene glycol macromonomer 6A as illustrated in FIG. 1.
2) Preparation of 2-aminoethyl-α-D-pyranmannoside as illustrated in FIG. 2.
3) Preparation of D-Mannose-containing styrene-PEG macromonomer from ω-carboxylic acid-styrene-PEG macromonomer and 2-aminoethyl-α-D-pyranmannoside as shown in FIG. 3.
4) Polymerization of styrene with the D-Mannose-containing styrene-PEG macromonomer according to a dispersion copolymerization protocol as shown in FIG. 4.

In another embodiment, a diverging approach may be utilized to prepare the nanoparticles. In a diverging approach, the polymeric core with the attached linking agents may be formed prior to the attachment of the biofunctional moiety to the surface of the nanoparticle. For example, FIG. 6 illustrates two possible mechanisms for polymerizing a polystyrene core with attached carboxylic acid-terminated PEG linking agents. FIG. 6A uses the ω-Carboxylic acid-styrene-polyethylene glycol macromonomer which can be prepared according to the process illustrated in FIG. 1. FIG. 6B uses a shorter carboxylic acid-terminated PEG macromonomer which can be prepared according to the mechanism illustrated in FIG. 5. In either case, polystyrene-PEG nanoparticles can be prepared via, for example, dispersion polymerization of the macromonomer with styrene, to form the corresponding non-biofunctionalized nanoparticles, as shown in FIG. 6.

According to the diverging approach, following formation of the non-biofunctionalized nanoparticles, the desired biofunctional moiety can be attached to the PEG linking compound at a functional group either at the terminus or elsewhere along the PEG chain. For example, in one embodiment, the biofunctional moiety can be a polypeptide sequence, such as, for instance, the tripeptide enkephalin (1-3 Tyr-Gly-Gly). In this embodiment, covalent attachment of the bioactive species can be attained via a carbodiimide-activated coupling reaction. In general, a carboxylic acid group on the linking agent can be an excellent platform for the attachment of the biofunctional moieties, though other functionalities on the linking agent could alternatively be utilized. For instance, in other embodiments, functionalities can include epoxy functionalities, amine functionalities, aldehyde functionalities, thiol functionalities, and the like.

The biofunctionalized nanoparticles of the invention can generally be anywhere from about 30 nm in average diameter up to several microns in average diameter. For instance, the nanoparticles can be between about 50 nm and about 1 micron in average diameter. For example, in one embodiment, nanoparticles can have an average diameter of about 250 nm. In another embodiment, the nanoparticles can have an average diameter of about 750 nm. The size of the nanoparticles can generally be controlled by standard methods as are known in the art including, for example, controlling the ratio between the individual components during polymerization, controlling the length of the polymeric chain component of the macromonomer, or through solvent selection.

The biofunctionalized material bound to the surface of the nanoparticles can include a material that is functionally identical to receptors recognized by the adhesins present on the target microorganism. As such, when the nanoparticles are in the presence of the target microorganism, the microorganism can recognize and bind to the biofunctionalized material on the nanoparticle. Many adhesins function as lectins, mediating microbial interactions with carbohydrate moieties of glycoproteins or glycolipids on host cell surfaces. Thus, in one embodiment, the biofunctional material of the disclosed nanoparticles can be a simple carbohydrate moiety or a functionalized derivative thereof, such as fucose, mannose, dextrose, mannan, galactose, or galactosamine, for example. Carbohydrate biofunctional moieties, among other advantages, are relatively inexpensive, non-toxic, and readily available. Other possible biofunctional materials that can be utilized in the present invention include specific amino acid moieties present in receptor proteins. Glycoproteins, glycolipids, or other components that can potentially serve as cellular surface receptors for adhesins can be utilized as the biofunctional materials of the present invention. Protein constituents of the ECM can also be utilized as biofunctional materials in those instances wherein the target microorganism communicates with the host via the ECM.

The biofunctional materials of the disclosed nanoparticles can be identically functional to receptors identified and bound by the surface adhesins of microorganisms that utilize an A/E attachment mechanism. This can include prokaryotic microorganisms, including both bacteria and cyanobacteria; eucaryotic microorganisms, including individual eucaryotic cells within an organism as well as parasites and the like, such as various amoebas, ciliates, flagellates, or sporozoans; viruses; or spores.

Many bacterial adhesins and their corresponding receptors are known in the art and may be targeted according to the present invention. See, for example, M. A. Mulvey & S. J. Hultgren, *Adhesin Bacterial*, Encyclopedia of Microbiology, Vol. 1, Academic Press, 42-47 (2000). For exemplary purposes only, the following table (Table 1) lists some of the possible biofunctional materials that may be utilized on the biofunctionalized nanoparticles of the present invention along with the corresponding adhesins and the bacterial pathogen which carries these specific adhesins. It should be noted that in certain instances, the receptor for a given adhesin may be an entire protein. In the present invention, the biofunctional material can generally include a polypeptide sequence of the protein that can be recognized and bound by the adhesin, and need not include the entire protein structure, though this is not prohibited in the disclosed nanoparticles.

TABLE 1

| Organism | Adhesin | Biofunctional Material |
|---|---|---|
| *Escherichia coli* | P pili (PapG) | Galα(1-4)Gal |
| | Type 1 pili (FimH) | D-mannose (uroplakin 1a & 1b, CD11, CD18, uromodulin) |
| | Curli (CsgA) | Fibronectin/ laminin/plasminogen |

TABLE 1-continued

| Organism | Adhesin | Biofunctional Material |
|---|---|---|
| | Prs pili | Galα(1-4)Gal |
| | S pili | α-sialyl-2,3-β-galactose |
| | K88 pili (K88ad) | IGLad (nLc$_4$Cer) |
| | K99 pili (FanC) | NeuGc(α(2-3)Galβ4Glc |
| | DR family | Decay |
| | DR | Accelerating |
| | DR-II | Factor |
| | AFA-I | (SCR-3 domain) |
| | AFA-II | |
| | F1845 | |
| | Nonfimbrial adhesins 1-6 | Glycophorin A |
| | M hemagglutinin | A$^M$ determinant of glycophorin A |
| | Intimin | Tir (EPEC encoded phosphoprotein) |
| Neisseria | Type-4a pili | CD46 |
| | Opa proteins | CD66 receptor family/HSPG |
| | Opa$_{50}$ | Vitonectin/fibronectin |
| | Opc | HSPG/Vitronectin |
| | LOS | ASGP-R |
| | Inducible adhesin | Lutropin receptor |
| Listeria monocytogenes | Internalin | E-cadherin |
| Haemophilus influenzae | Hemagglutinating pili | AnWj antigen/lactosylceramide |
| | Hsp-70-related proteins | Sulfoglycolipids |
| | HMW1, HMW2 | Negatively charged Glycoconjugates |
| Campylobacter jejuni | CadF | Fibronectin |
| Yersinia | Invasin | β1 integrins |
| | YadA | Cellular fibronectin/collagen/laminin |
| Bordetella pertussis | FHA | CR3 integrin |
| | Pertactin, BrkA | Integrins |
| | Pertussin toxin | Lactosylceramides/gangliosides |
| Mycobacterium | BCG85 complex, FAP proteins | Fibronectin |
| Streptococcus | Protein F family | Fibronectin |
| | Polysaccharide capsule | CD44 |
| | ZOP, FBP4, GAPDH | Fibronectin |
| | Lipoteichoic acid (LTA) | Fibronectin/macrophage scavenger receptor |
| | M protein | CD46/fucosylated glycoconjugates/fibronectin |
| Staphylococcus | FnbA, FnbB | Fibronectin |
| | Can | Collagen |
| | Protein A (Spa) | von Willebrand factor |
| | ClfA | Fibrinogen |
| | EbpS | Elastin |

This exemplary table of biofunctional materials is non-limiting, and microorganisms that can be targeted by the biofunctionalized nanoparticles of the present invention can include these as well as many other bacteria including, for example, bacteria in the genera *Campylobacter, Listeria, Salmonella, Shigella, Vibrio, Aeromonas, Moraxella, Escherichia* and *Helicobacter*. Major enteropathogenic species that can be specifically targeted by the present invention can include *Salmonella typhi, Enterobacter aerogenes, Streptococcus faecalis, Neisseria gonorrhoeae, Neisseria meningitidis, Pseudomanas aeruginose, Dichelobacter nodus, Vibrio parahaemolyticus, Yersinia enterocolitica, Vibrio cholerae* 01, *Vibrio cholerae* 0139, non-01 *Vibrio cholerae, Vibrio fluvialis, Aeromonas hydrophila*, and *Plesiomonas shigelloides*.

In one embodiment, the nanoparticles of the present invention can target commensal microorganisms such as yeast or other fungi. For example, the yeast *Candida albicans* is a human commensal. The ability of Candida to adhere to the host is a fungal virulence factor similar to that of other microbial systems, and is considered a significant step in the development of candidiasis. The present invention can also target viral pathogens. In particular, the biofunctional materials on the surface of the nanoparticles can include those which can be recognized and bound by the pathogenic capsid surfaces of a virus. For example, the nanoparticles can be biofunctionalized so as to target various rotaviruses, Norwalk-like viruses, adenoviruses, astroviruses, coronaviruses, enteroviruses, or other viral agents. For example, in one embodiment, nanoparticles can be biofunctionalized with the GP120 protein of HIV to provide a particulate immunizing preparation.

Exemplary eucaryotic enteropathogens that can be targeted by the present inventions include the parasites *Giardia intestinalis, Entamoeba histolytica, Cryptosporidium parvum, Cycolsporocayetanensis, Dientamoeba fragilis, Isospora belli, Balantidium coli*, and *Strongyloides stercoralis*.

In one embodiment, the compositions of the present invention can prevent infection of a host by a pathogenic microorganism by eliminating the bioactivity of the pathogen through binding the pathogen to the nanoparticle. For example, the nanoparticles of the invention can irreversibly bind to the targeted pathogens at the adhesins and mask those particular adhesins, preventing the pathogen from binding to host cells and infection of the host. The nanoparticles of the present invention can, in some embodiments, be quite large in relation to many of the pathogenic microorganisms to which they can bind. Therefore, the presence of the nanoparticles irreversibly bound to the surface of the pathogenic microorganism can, in these embodiments, sterically hinder binding and subsequent invasion of a host cell by the microorganism.

In one embodiment, the compositions of the present invention can be utilized to agglomerate microorganisms. The biofunctionalized nanoparticles will generally have multiple biofunctional material components across the surface of the nanoparticles, with estimates of numbers of individual biofunctional moieties attached to the surface of the nanoparticles in the tens of thousands. In addition, the microorganisms themselves have multiple adhesins across their surfaces. The natural ligand-receptor systems in nature are high-affinity binding systems. Thus, when the compositions of the invention are in the presence of multiple microorganisms, as would be expected in an area contaminated with the microorganism, a single nanoparticle can bind to more than one microorganism. In addition, a microorganism that is already bound to a nanoparticle at one adhesin location can bind to another nanoparticle at another adhesin site should the two come into proximity. In this manner, as the nanoparticles and microorganisms continue to contact each other and bind to one another, large aggregate complexes of the two can be formed. Formation of aggregates of the nanoparticles with the microorganisms can eliminate the bioactivity of the microorganism through both steric hindrance and adhesin masking. In addition, experimental results indicate that the formation of large aggregates can lead to the death of the microorganisms.

The formation of the large agglomerated complexes can not only prevent infection of a host by the microorganisms, as described above, but can also provide a means for gathering, identifying, or removing the microorganisms from a location.

The nanoparticles of the present invention can have many different practical applications, a few of which are discussed in more detail below.

Purging

In one embodiment, the process of the present invention can be utilized to purge a pathogenic microorganism from a person or an animal that is already infected by or a carrier of a pathogenic microorganism. In this embodiment, a composition including the nanoparticles can be ingested by the individual to form agglomerated complexes with the microorganisms in the digestive tract.

For example, the composition can be an aqueous composition including the suspended nanoparticles that is simply swallowed by the individual. Alternatively, the composition can include encapsulated nanoparticles or nanoparticles otherwise prepared for release following ingestion within the digestive system at a time or location where the targeted microorganisms can be expected to be encountered. Upon contact between the two, the microorganisms and the nanoparticles can form agglomerated complexes within the digestive tract. The large agglomerated complexes can be removed from the digestive tract via the natural peristalsis of the individual at a rate dependent on intestinal transit time.

In some embodiments, infection of the individual by a pathogenic microorganism may have already begun prior to ingestion of the disclosed compositions. For instance, individual microorganisms may already be bound to the surface of the digestive tract at the time the composition including the biofunctionalized nanoparticles comes into contact with the microorganisms. In this embodiment, agglomerated complexes can form at the surfaces where the pathogens have attached themselves to the walls of the digestive tract. The formation of the agglomerated complexes can still remove the microorganisms from the digestive tract, even in this embodiment, as the shear forces of intestinal contents acting on the agglomerated complexes during peristalsis can physically wrench the infecting agents from the walls of the digestive tract.

In one preferred embodiment, the compositions of the present invention can be utilized to prevent enteric disease in humans brought about by infection by any of a variety of enteropathogens that can be carried by consumable livestock. In general, in this embodiment, infection can be prevented by decontaminating or purging the source or carrier of the pathogens prior to processing and human ingestion.

For example, in one embodiment, the present invention is directed to the prevention of gastroenteritis cause by bacterial infection by C. jejuni. C. jejuni is the leading cause of bacterial enteric infection in the United States and Europe. While C. jejuni is not carried by healthy individuals, it is often isolated from healthy cattle, poultry, and even flies. It is also sometimes present in non-chlorinated water sources. The most common source of C. jejuni infection in the United States is chicken. Human feeding studies in the past have suggested that only about 400 to 500 bacteria can initiate clinical infection in some individuals, though this can obviously vary from host to host.

In modern chicken processing plants, a single plant may process several thousand chickens a day. Loads of chickens are delivered to a plant from many different sources over the course of a single day. Though the entire plant is often decontaminated on a daily basis to prevent the spread of bacterial infection, unfortunately, if a single load of C. jejuni infected animals passes through the plant, it is practically impossible to prevent the spread of the bacteria throughout the processing line over the course of the day. Food products delivered from the contaminated processing line can then carry the pathogen and can lead to human infection.

In one preferred embodiment, the present invention is directed to a process for purging infected animals of pathogenic microorganisms before they reach a processing plant. For instance, the compositions of the present invention can be utilized to purge the C. jejuni bacteria from chickens prior to transport to a processing plant. In this embodiment, compositions of the invention can be fed to the chickens prior to transport. For instance, chickens can be gavaged prior to transport to a processing plan with a composition including a suspension of nanoparticles as herein described. The nanoparticles in this case could incorporate biofunctional materials specifically targeted for the C. jejuni bacteria. For example, biofunctionalization of the nanoparticles with a D-mannose moiety can be utilized to agglomerate certain strains of C. jejuni within the digestive tract of an animal such as chickens carrying the pathogen.

In general, a composition comprising between about 50 mg and 200 mg D-mannose biofunctionalized nanoparticles per kg of body weight may be ingested by an animal. In one embodiment, the composition can comprise about 100 mg D-mannose biofunctionalized nanoparticles per kg body weight.

Following ingestion, the D-mannose biofunctionalized nanoparticles of the present invention can bind to C. jejuni within the digestive tract of the chicken, and large agglomerated complexes of bacteria and nanoparticles can form which can pass through the chicken via natural peristalsis. This can be done so as to purge C. jejuni from the animals prior to the arrival of the chickens at the processing plant.

In general, a chicken has a digestive retention time of about 200 minutes (see, for example, J. L. Grimes, et al., Journal of Poultry Research, Vol. 6, No. 4, p. 339, 1997). Thus, targeted pathogens within the digestive tract could be largely purged from the animals within about 3-4 hours of ingestion, depending on individual digestive retention time. Following this period, and providing the animals are kept away from any source of recontamination of the pathogens, levels of the pathogens within the digestive tract of the animals could remain greatly diminished until the time of processing.

Though described here in some detail for the enteropathogen C. jejuni, it should be understood that the purging processes of the present invention may be equally applicable to other pathogens and other carriers to prevent human infection by the pathogens via human consumption. For instance, similar to C. jejuni, certain pathogenic E. coli has exhibited strong adhesin-specific interactions with D-mannose molecules. As such, in certain embodiments of the present invention, D-mannose biofunctionalized nanoparticles can be utilized to aggregate E. coli bacteria in the prevention of E. coli enteroinfection similar to the process described above for the prevention of C. jejuni enteroinfection.

Decontamination

In another embodiment, the formation of large agglomerated complexes of the nanoparticles of the present invention with microorganisms can be utilized to decontaminate an area. For instance, in one embodiment, the nanoparticles can be biofunctionalized to target microorganisms which can be considered a danger to the general public such as through contamination of personnel, buildings (interior or exterior), equipment, soil, water, or vegetation. In this particular embodiment, the nanoparticles can be spread over the contaminated area, such as in a powder or spray form, so as to contact the microorganisms and form large, agglomerated complexes. These complexes can be large enough so as to be simply swept, vacuumed, or otherwise removed from the contaminated area.

Treatment through Increased Specificity

In one embodiment, the nanoparticles of the present invention can be biofunctionalized with a combination of different biofunctional materials. This can provide increasing levels of specificity of the nanoparticles to a specific microorganism. A single microorganism can often include multiple adhesins on the surface, with varying receptor specificities. In addition, the different adhesins on the surface of a single microorganism can often function synergistically. For example, many different microorganisms could be expected to bind to nanoparticles biofunctionalized with a monosaccharide such as mannose or galactose, for example, as these are fairly common receptors for a wide variety of adhesins. Greater binding specificity could be obtained by the nanoparticles by including combinations of receptor structures on the surface, where the combination of structures can be recognized only by the targeted microorganism.

For example, in one embodiment, a polyethylene based linking agent can be synthesized with multiple residue-like side groups placed precisely along the backbone chain. Similarly, different biofunctional materials can be placed on different linking agents across the surface of the nanoparticle. Either or both of these approaches in concert can provide a protein-like synthetic macromolecular structure on the surface of the nanoparticle that is similar in structure to natural host proteins to which the microorganism can adhere. The nanostructure obtained can have structural and functional specificity to a specific target microorganism. This design can maximize the probability for the nanoparticles to bind to protein structures on the targeted microorganisms with very specific high-affinity binding.

In either case, a more natural protein-like surface can be formed on the nanoparticle which can be more specifically recognized and bound by the targeted microorganisms, while avoiding binding to other, non-targeted microorganisms. For example, in one embodiment, the nanoparticles of the present invention may be utilized to treat an existing infection, such as an existing enteroinfection, for example. In this embodiment, the biofunctionalized nanoparticles can be specifically designed so as to target and bind the infective agents, but avoid binding to other microorganisms in the alimentary canal, microorganisms which may be necessary for the health of the individual.

Identification

In another embodiment, the nanoparticles can be labeled with a fluorescent label such as fluorescein isothiocyanate. The labeled nanoparticles can then be used to identify microorganisms bearing adhesins to which they bind. For example, fluorescent-labeled nanoparticles can be utilized to identify pathogens in biological samples. In this embodiment, the nanoparticles can bind to and thus label pathogens in biological samples such as autopsies, biopsies, urine samples, oral swabs, fecal smears or sputum samples. The targeted pathogens can be infectious agents, such as enteropathogenic bacteria or parasites. Alternatively, the labeled nanoparticles can be targeted toward endogenous entities that are indicative of disease, such as cancer cells, for example, or agents which can be found in a biological sample that may be a byproduct of a disease process. Thus, the compositions of the present invention can in this embodiment be used for diagnoses of disease or recognition and identification of the presence of disease-causing agents or their products.

In another embodiment, the labeled nanoparticles can be utilized to identify places or areas that are contaminated by a suspected pathogenic microorganism. In this embodiment, the labeled nanoparticles can also be utilized to estimate the level of contamination by the number and size of agglomerated complexes in a given area. For example, samples can be taken from an industrial site suspected of being contaminated by a known pathogen. Water, plant, and soil samples can be exposed to nanoparticles of the invention that have been biofunctionalized to be recognized and specifically bound by adhesins on the surface of the suspected pathogen.

In another embodiment, the labeled nanoparticles of the present invention can be used to identify unknown adhesins on the surface of a microorganism. For example, nanoparticles including a label and a known biofunctional moiety can be exposed to a microorganism. Adhesins on the microorganism can be identified by observing binding affinity for the microorganism to the labeled nanoparticles.

Fluorescent labeling of compounds is generally known in the art and thus is not described in detail herein. Fluorescent labels that can be incorporated into the biofunctionalized nanoparticles include cross-linking agents in the polymeric core of the nanoparticles or fluorescent probes attached to the surface of the nanoparticles. For example, anthracene, which is a strongly fluorescent molecule, can be employed as a cross-linking agent in a polymerization process. Similarly, divinyl porphyrins, which are strongly fluorescent in the extreme red to near-infrared wavelength regions (650-850 nm) can be used as crosslinking agents in the nanoparticles.

Luminescent probes attached to the surface of the nanoparticles can be attached similar to the biofunctional materials in formation of the nanoparticles. Though not required, in some embodiments the biofunctional materials can be loaded onto the nanoparticles in relatively high concentrations prior to attachment of the labels. The fluorescent probes can then be incorporated in lower concentration so as to avoid interference with the affinity of the nanoparticles for the microorganism adhesin sites. For example, the fluorescent probes can be in a ratio to the biofunctional moieties of between about 1:50 to about 1:150.

The selection of specific luminescent probes can depend at least in part upon the desired application of the nanoparticles. For example, in tracing and analysis of enteropathogens in biological samples (such as biopsies or fecal smears, for instance), light transmission through the biological environment is a major consideration. Possible luminescent probes that can be incorporated into the nanoparticles can include, for example, porphyrins, FITC, and anthracene.

In one embodiment, derivatized phathlocyanines and metellophathlocyanines can be utilized as fluorescent probes. For example, diimide-catalyzed amidation and esterification chemistries can be used to link derivatized fluorescent probes to the nanoparticles, as is generally known in the art.

Drug Delivery

In another embodiment, the nanoparticles can be utilized as a delivery vehicle for an agent such as a vaccination agent to a biological system.

There are three basic requirements for a successful vaccination process: long biological half-life of the vaccine, the ability to induce an antibody response to a native challenge, and the establishment of a long-term response. In one embodiment of the present invention, an antigenic epitope such as, for example, a purified viral capsid component, can be attached to the biofunctionalized nanoparticles to create a preparation that includes immunogenic particles similar in size to the native virus. Particulate antigens in general have the potential for much longer biological half-life than those of soluble antigens. Thus, the particulate vaccine can be retained within the recipient's system for a longer period of time. In this embodiment, the particulate vaccine can be prevented from rapidly diffusing from the site of entry and the process can diminish the rate of excretion for the vaccine. This extended biological half-life of the vaccine agent within the host can increase the likelihood of a strong antibody response by the host, and subsequently can lengthen the protective term in the host. This is one manifestation of the adjuvant effect (an example is the precipitation of bacterial toxins by alum to create an insoluble antigenic form that is released slowly over months). In addition, in this embodiment, the nanoparticle-derived antigen could have a stronger opsonizing (macrophage-stimulating) potential than that of the same antigen in the soluble state, since macrophages respond more avidly to particulate antigens.

In yet another embodiment, nanoparticles could serve as carriers for peptides too small to be immunogenic in themselves. This strategy is analogous to earlier demonstrations of the hapten-carrier phenomenon. Haptens are small organic molecules that are antigenic, but not immunogenic. When haptens are complexed to large molecules such as proteins, they function as the immunodominant epitope of the hapten-carrier conjugate. Many biologically important substances, including drugs, peptide hormones, and steroid hormones can function as haptens. Use of this phenomenon has been widespread in radioimmunoassay testing for prohibited drug use in athletes and racehorses.

The compositions of the present invention can also include other biologically active agents, in addition to the biofunctionalized nanoparticles as herein described. For instance, in one embodiment, the nanoparticles can be utilized in conjunction with antibiotic agents to improve the efficacy of the antibiotic.

The use of antibiotic agents can sometimes lead to undesired side effects. For example, in meningococcal infections, when the bacterial pathogen is lysed by an antibiotic, the bacteria release endotoxins into the circulatory system of the infected host. The free endotoxins can then cause undesired effects as they spread through the host and exacerbate the inflammatory response. In this embodiment, biofunctionalized nanoparticles that target the released endotoxins can be used in conjunction with the antibiotics. Thus, the nanoparticles can bind the endotoxins that are released as the bacteria lyse and thus can prevent spread of the endotoxins through agglomeration, masking, and/or steric hindrance. As the biofunctionalized nanoparticles can be designed with high affinity for the specific endotoxins, they can bind to and hold the disease causing agents until the agents are either degraded or destroyed with the nanoparticles by the body's natural defense systems or excreted from the system.

The present invention may be better understood with reference to the following examples.

EXAMPLE 1

The macromonomer labeled 6A in FIG. 1 was prepared according to the formation process illustrated therein.

Materials. p-Chloromethylstyrene (90%), 4-dimethylamino pyridine (DMAP, 99%), hydrochloric acid, N-hydroxysuccinimide (93+%), MES hydrate (99%), nitrobenzene (99%), pyridine (99%), sodium hydride (NaH, 60% dispersed in mineral oil), sodium bicarbonate (powder), and succinic anhydride (99%) were purchased from Acros, azobisisobutyronitrile (AIBN, 98%) and polyethylene glycol methacrylate ($M_n$~526) from Aldrich, 1-ethyl-3-(3-dimethylamino)propylcarbodiimide hydrochloride (EDAC), triphenylphosphine (99%), sodium azide (99%), and p-toluenesulfonyl chloride (98%) from Alfa Aesar, styrene from Baker, polyethylene glycol ($M_w$~2000) from Fluka, and tetrabutylammonium bromide (98%) from Lancaster. Ethanol, chloroform, and diethyl ether were purchased from Fisher and used without further purification. THF was distilled over sodium, and methylene chloride was distilled over calcium hydride before use. DMF was distilled over calcium hydride under reduced pressure before use. Deuterated water (99.9%) and chloroform for NMR measurements were obtained from Cambridge Isotope Laboratories.

Preparation of Hydroxy-St-PEG Macromonomer (Macromonomer A on FIG. 1). NaH (0.6 g, 15 mmol) was added to a mixture of polyethylene glycol ($M_w$~2000, 20 g, 10 mmol) and THF (100 mL). After being kept at 40° C. for 4 h, the reaction mixture was cooled to 34° C., added with p-chloromethylstyrene (1.83 g, 12 mmol), kept at 30° C. for 24 h, and then added with HCl until neutral pH. The resulting solution was concentrated and precipitated into cold ether, followed by filtration for the solids and drying in a vacuum oven at room temperature to obtain A (20.1 g, 95% yield). $^1$H NMR (500 MHz, CDCl$_3$): 7.38 (d, 2H), 7.30 (d, 2H), 6.72 (m, 1H), 5.74 (d, 1H), 5.24, (d, 1H), 4.65 (s, 2H), 3.4-4.0 (m, 180H) ppm. C NMR (125 MHz, CDCl$_3$): 137.95, 136.99, 136.60, 128.01, 126.26, 113.82, 73.00, 72.60, 70.41, 69.45, 61.78 ppm.

Preparation of Tosylate-St-PEG Macromonomer (Macromonomer B on FIG. 1). Macromonomer A (10 g, 4.3 mmol) was dissolved in dry CH$_2$Cl$_2$, followed by the addition of pyridine (5.2 g, 65 mmol). The mixture was cooled to 0° C., and then p-toluenesulfonyl chloride (12.65 g, 65 mmol) was added. The resulting mixture was stirred at room temperature for 12 h. After CH$_2$Cl$_2$ was removed on a rotary evaporator, to the resulting oil were added CHCl$_3$ (20 mL) and H$_2$O (10 mL). The organic layer was washed with HCl (2 M), aqueous NaHCO$_3$ (5%), and then H$_2$O. It was dried with MgSO$_4$ powder, filtered, and precipitated into cold ether. The filtration for the solids was followed by washing with cold ether several times and drying in a vacuum oven at room temperature to obtain B (9.5 g, 92% yield). $^1$H NMR (500 MHz, CDCl$_3$): 7.78 (d, 2H), 7.30 (m, 6H), 6.69 (m, 1H), 5.72 (d, 1H), 5.22 (d, 1H), 4.54 (s, 2H), 4.13 (t, 2H), 3.48-3.40 (m, 180 H), 2.44 (s, 3H) ppm. C NMR (125 MHz, CDCl$_3$): 144.83, 137.95, 136.96, 136.59, 133.04, 129.89, 128.03, 127.99, 126.25, 113.81, 70.78, 70.69, 70.61, 69.44, 68.90, 68.50, 21.71 ppm.

Preparation of Azide-St-PEG Macromonomer (Macromonomer C on FIG. 1). Macromonomer B (8.9 g, 4.2 mmol) was dissolved in DMF (60 mL), and to the solution was added NaN$_3$ (2.76 g, 42 mmol) and tetrabutylammonium bromide (0.2 g, 0.54 mmol). After being kept at 40° C. for 4 h, the mixture was precipitated into cold ether to remove DMF. The resulting solids were re-dissolved in CHCl$_3$, and the solution was dried with MgSO$_4$. Upon filtration to remove MgSO$_4$, the CHCl$_3$ solution was concentrated and again precipitated into cold ether, followed by the filtration again and drying in a vacuum oven at room temperature to obtain C (8.3 g, 95% yield). $^1$H NMR (500 MHz, CDCl$_3$): 7.78 (d, 2H), 7.30 (d, 2H), 6.69 (m, 1H), 5.72 (d, 1H), 5.22 (d, 1H), 4.54 (s, 2H), 3.80-3.54 (m, 180 H), 3.38 (t, 2H) ppm. C NMR (125 MHz, CDCl$_3$): 137.95, 137.00, 136.60, 128.02, 126.28, 113.84, 73.00, 70.63, 68.90, 68.50, 50.74 ppm.

Preparation of Amine-St-PEG Macromonomer (Macromonomer D on FIG. 1). Macromonomer C (3 g, 1.38 mmol), PPh$_3$ (4.4 g, 16.5 mmol), and H$_2$O (37.3 mg, 2.1 mmol) were mixed with THF (2.5 mL), and the mixture was stirred at room temperature for 36 h. The reaction mixture was concentrated and precipitated into cold ether, followed by filtration for the solids and drying under vacuum at room temperature to obtain D (2.6 g, 94% yield). $^1$H NMR (500 MHz, CDCl$_3$): 7.39 (d, 2H), 7.30 (d, 2H), 6.71 (m, 1H), 5.76 (d, 1H), 5.25 (d, 1H), 4.57 (s, 2H), 3.8-3.4 (m, 180H), 2.88 (t, 2H) ppm. C NMR (125 MHz, CDCl$_3$): 137.94, 136.97, 136.59, 127.99, 126.25, 113.18, 73.10, 72.98, 70.60, 69.44, 41.83 ppm.

Preparation of Macromonomer 6A. Macromonomer D (1.96 g, 9.2 mmol), succinic anhydride (0.18 g, 18.4 mmol), and DMAP (10 mg, 0.08 mmol) were dissolved in CH$_2$Cl$_2$ (20 mL), and the solution was stirred at room temperature for 36 h. Water (5 mL) was added to quench the reaction. The solution was washed with water (5 mL×3), and the organic layer was dried with MgSO$_4$ and filtered. The resulting solution was concentrated and precipitated into cold ether, followed by filtration for the solids and drying under vacuum at room temperature to obtain 1 (1.63 g, 80% yield). $^1$H NMR (500 MHz, CDCl$_3$): 7.40 (d, 2H), 7.34 (d, 2H), 6.27 (m, 1H), 5.76 (d, 1H), 5.26 (d, 1H), 4.58 (s, 2H), 3.90-3.40 (m, 180H), 2.67 (t, 2H), 2.56 (t, 2H) ppm. C NMR (125 MHz, CDCl$_3$): 174.34, 172.67, 137.92, 136.58, 128.00, 126.25, 113.83, 72.00-68.00 (m), 31.03, 30.27 ppm.

EXAMPLE 2

Figure 5:
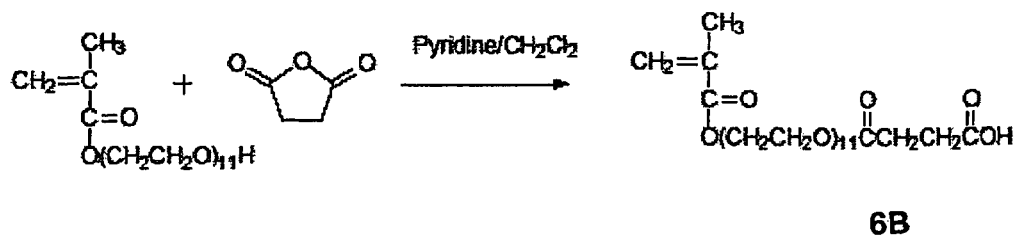
FIG. 5 is a formation mechanism for a carboxylic acid terminated PEG macromonomer that can be utilized in forming biofunctionalized nanoparticles of the present invention.
Figure 6:
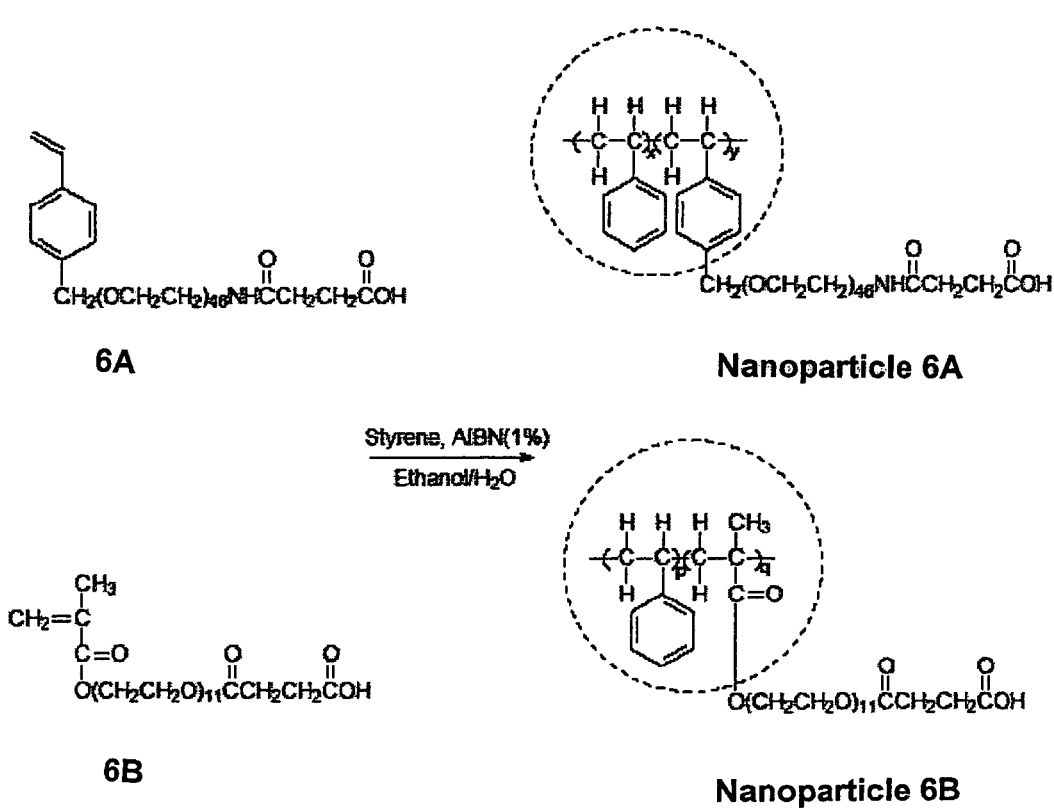
FIG. 6 illustrates two divergent approach formation mechanisms for biofunctionalized nanoparticles, one mechanism from the carboxylic acid terminated styrene-PEG macromonomer of FIG. 1 (nanoparticles 6A) and the other from the carboxylic acid terminated PEG macromonomer of FIG. 5 (nanoparticles 6B)

The macromonomer labeled 6B in FIG. 5 was prepared according to the formation process illustrated therein.

Materials as described above in Example 1 were used. Succinic anhydride (5 g, 50 mmol), pyridine (50 mmol), and nitrobenzene (20 drops) were added to a solution of polyethylene glycol methacrylate (5.26 g, 10 mmol) in CH$_2$Cl$_2$ (200 mL). After refluxing at 55° C. for 48 h, the solvent CH$_2$Cl$_2$ was removed on a rotary evaporator, and the solids were dissolved in an aqueous sodium bicarbonate solution (10%). The resulting solution was filtered to remove solid residues and then washed with diethyl ether (25 mL×3) to collect the organic layer. The resulting diethyl ether solution was cooled to 0° C. and acidified with HCl, followed by the extraction with CHCl$_3$. The CHCl$_3$ solution thus obtained was washed with water and then dried with MgSO$_4$. Upon the filtration to remove MgSO$_4$ and then the evaporation to remove CHCl$_3$, Macromonomer 6B was obtained as a yellow oil (5.95 g, 95% yield). $^1$H NMR (500 MHz, CDCl$_3$): 6.03 (s, 1H), 5.48 (s, 1H), 4.27 (t, 2H), 4.23 (t, 2H), 3.54 (br, 36H), 2.5 (m, 4H), 1.83 (s, 3H) ppm. C NMR (125 MHz, CDCl$_3$): 176.8, 172.3, 167.5, 136.4, 125.9, 70.7, 69.2, 63.9, 29.0, 28.9, 18.4 ppm.

EXAMPLE 3

In this example, nanoparticles including a polystyrene core and linking agents of carboxylic acid-terminated oligomeric polyethylene glycols were first synthesized via dispersion polymerization. The polymeric nanoparticles were then covalently functionalized with enkephalin peptide molecules in the carbodiimide-activated coupling reaction to form biofunctionalized nanoparticles according to a diverging approach.

Materials: Enkephalin (1-3 Tyr-Gly-Gly) was purchased from Sigma, Nhydroxysuccinimide (93+%) and MES hydrate (C$_6$H$_{13}$NO$_4$SCH$_2$O, 99%) from Acros, azobisisobutyronitrile (AIBN, 98%) from Aldrich, 1-ethyl-3-(3-dimethylamino)propylcarbodiimide hydrochloride (EDAC) from Alfa Aesar, and ethanol from Fisher. Deuterated water (99.9%) and chloroform (99.8%) for NMR experiments were supplied by Cambridge Isotope Laboratories. Biuret reagent and Folin and Ciocalteu's phenol reagent for the modified Lowry assay were obtained from Sigma.

Dynamic light scattering measurements were carried out on a Coulter N4 Plus particle sizer. NMR measurements were performed on a JEOL Eclipse +500 NMR spectrometer. TEM analyses were conducted on a Hitachi H7000 TEM system. UV/vis absorption spectra were recorded on a Shimadzu 3100 spectrophotometer.

Macromonomers 6A and 6B were prepared as described above in Examples 1 and 2. The macromonomers were then independently utilized to form polystyrene-PEG nanoparticles via the dispersion polymerization of each macromonomer with styrene as illustrated in FIG. 6. In a typical reaction, styrene (1.042 g, 10 mmol) and either macromonomer 6A or 6B (1.1 g, 0.5 mmol) were added to an ethanol/water mixture (4/1, 25 mL). The mixture was cooled to 0° C., and to the mixture was added AIBN (16 mg, 0.1 mmol). Upon degassing, the mixture was stirred at 60° C. for 24 h, yielding a milky suspension. The suspension was transferred into a membrane tubing (cut-off molecular weight 12,000) for dialysis against fresh deionized water for 3 days to yield a purified aqueous suspension of the nanoparticles formed according to the formation mechanism illustrated in FIG. 6. The two different nanoparticles obtained, depending upon the starting macromonomer, are herein referred to as nanoparticle 6A and nanoparticle 6B.

The dispersion copolymerizations of the illustrated macromonomers 6A and 6B with styrene yielded polymeric nanoparticles 6A and 6B, respectively, in aqueous suspensions. The suspensions appeared milky, but remained stable essentially indefinitely. Each nanoparticle had a polystyrene core and a shell of hydrophilic PEG chains that were terminated with carboxylic acids. Such a structural arrangement is believed to be responsible for the stability of the aqueous suspensions.

The dynamic light scattering results of the suspensions are shown in Table 1.

TABLE 1

| Nano-particle | Average Diameter Via Light Scattering before Functionalization (nm) | Average Diameter ViaTEM before Functionalization (nm) | Average Diameter Via Light Scattering After Functionalization (nm) |
|---|---|---|---|
| 6A | 175 (25) | 160 (18) | 174 (21) |
| 6B | | 180 (20) | 190 (60) |

Note:
the number in parenthesis is the standard deviation.

Figure 7:
FIG. 7 is a transmission electron microscopy (TEM) image of the polystyrene core of a nanoparticle with PEG linking agents attached, prior to biofunctionalization.

The nanoparticles obtained were of relatively narrow size distributions. The formation of nanoparticles and their average sizes and size distributions are confirmed by the results from TEM characterizations. Shown in FIG. 7 is a typical TEM image of the nanoparticle 6B. The halo surrounding each particle may be attributed to the PEG shell. The average sizes determined from the TEM images are slightly smaller than those obtained from the dynamic light scattering experiments (Table 1). This seems understandable because the dynamic light scattering measures hydrodynamic volumes of the nanoparticles, corresponding to a more expanded surface structure of the nanoparticles in a suspension. Between the two nanoparticle samples, the difference in their average sizes has to do with the PEG chain length in the starting macromonomers. The macromonomer with a longer PEG chain (macromonomer 6A) corresponds to smaller particles, while the macromonomer of a shorter PEG chain (macromonomer 6B) corresponds to larger particles.

To form biofunctionalized nanoparticles 6A, MES hydrate was added to an aqueous suspension of nanoparticle 6A (10 mL, 5.2 wt % nanoparticles 6A, 3 mole % —COOH on the nanoparticles) to result in the buffer condition (0.1 M) of pH equal to 5.6, followed by the addition of N-hydroxysuccinimide (15 mg) and EDAC (30 mg). The suspension was stirred at room temperature for 3 h. The mixture was centrifuged to remove the MES buffer, washed with a phosphate buffer twice, and suspended in the phosphate buffer (10 mL). To the suspension was added enkephalin (60 mg, 0.2 mmol). The resulting suspension was stirred at room temperature for 24 h, followed by dialysis (membrane tubing cut-off molecular weight 12,000) against fresh deionized water for 3 days.

The same process was utilized to formed enkaphalin biofunctionalized nanoparticles 6B from an aqueous suspension of nanoparticles 6B.

The functionalization of the polymeric nanoparticles with the peptide Tyr-Gly-Gly resulted in no meaningful changes in the size characterizations. The dynamic light scattering and TEM results were essentially unchanged from those of the nanoparticles before the peptide functionalization. This also seems reasonable considering the small size of the peptide.

Following formation, the nanoparticle samples were dissolved in organic solvents, resulting in the destruction of the nanoparticles because of the solubility of the polystyrene copolymers. The resulting homogeneous solutions in deuterated chloroform were used in NMR measurements. The solution-phase $^1$H NMR spectra thus obtained were not very informative because they were overwhelmed by the extremely broad signals in the aromatic region arising from polystyrene, as well as broad peaks resulting from the polymer corona. The relatively low peptide content overall in the nanoparticle sample also makes the solution-phase NMR characterization virtually impossible. Thus, the gel-phase NMR approach was employed to characterize the peptide-functionalized polymeric nanoparticles in an aqueous suspension.

Figure 8:
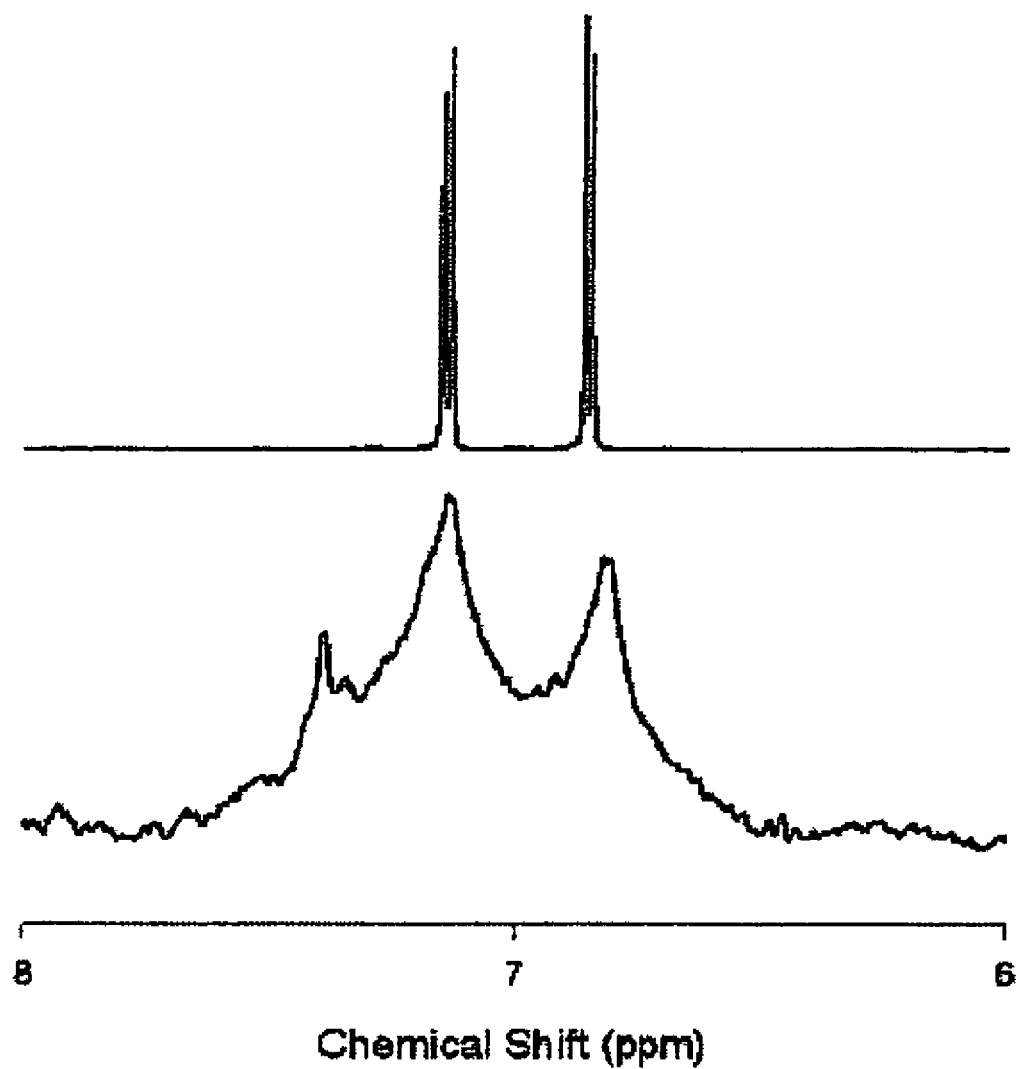
FIG. 8 is $^1H$ NMR spectra in the aromatic region for enkaphalin in $D_2O$ solution (top) and for enkaphalin functionalized nanoparticles 6A in concentrated aqueous suspension (bottom)

The gel-phase NMR measurements were carried out with the same NMR probe as for solutions, except that highly concentrated nanoparticle suspensions were used. As shown in FIG. 8 top, the proton NMR spectrum of the peptide-attached nanoparticles 6A in an aqueous ($D_2O$) suspension consisted of broad signals in the aromatic region in addition to the strong peaks associated with the protons in the PEG corona of the nanoparticles, but there were no meaningful contributions from the polystyrene core. The aromatic signals may be attributed to the phenyl protons in the tyrosine unit of the peptide, in comparison with the sharp signals observed in the same region for the peptide in solution (FIG. 8 top).

In the gel-phase $^1$H NMR spectrum of nanoparticles 6A without peptide attachment (FIG. 8, bottom), there are the same strong peaks associated with the protons in the PEG corona of the nanoparticles, but no aromatic signals. The comparison of $^1$H NMR results in FIG. 8 provides strong evidence that the peptide species are indeed attached to the polymeric nanoparticles.

More quantitatively, the peptide species attached to the polymeric nanoparticles were analyzed by using the modified Lowry assay. The assay is commonly used in the determination of peptide and protein contents through targeting the tyrosine or tryptophan moiety. The testing procedure involves the mixing of the specimen with the Biuret reagent and then Folin and Ciocalteu's phenol reagent. The tyrosine or tryptophan moiety was detected when the colorless solution turned blueish green, with the extent of the color change (absorbance around 725 nm in the visible absorption spectrum) corresponding to the tyrosine or tryptophan concentration. The presence of a tyrosine unit in enkephalin (1-3) makes the peptide-functionalized polymeric nanoparticles responsive to the assay. A standard curve was obtained by using solutions of free peptide. In order to match the effects of light scattering on the absorption measurements, these solutions for the standard curve were also added with the same amount of unfunctionalized nanoparticles as the estimated nanoparticle content in the sample solution for determination. The result thus obtained for the peptide-functionalized nanoparticles 6A was 0.01 mg peptide per mg nanoparticles. By using the average diameter obtained from the TEM analysis (Table 1) for the spherical polystyrene core, with the same density of 1.047 g/cm$^3$ as for bulk polystyrene, the average number of PEG linkers per nanoparticle and the average total mass per nanoparticle were estimated as 395,000 linkers/particle and $3.6 \times 10^{12}$ mg/particle, respectively. Thus, the average number of peptide species per nanoparticle is 73,000, which corresponds to ~20% of the PEG tethers on the nanoparticle.

EXAMPLE 4

In this example, nanoparticles covalently attached with derivatized D-mannose molecules were prepared according to the converging approach illustrated in FIGS. 2-4. 2-aminoethyl-α-D-pyranmannoside was first prepared as illustrated in the formation scheme of FIG. 2. A styrene macromonomer substituted with the derivatized D-mannose was then prepared according to the formation mechanism of FIG. 3.

The nanoparticles were then prepared in dispersion copolymerization of styrene and the styrene macromonomer p-substituted with derivatized D-mannose according to a converging polymerization approach as herein described and illustrated in FIG. 4.

The nanoparticles thus prepared were used to study adhesion interactions with *E. coli* ORN178 (provided by Dr. Chu-Cheng Lin, Department of Zoology, National Taiwan Normal University, Taiwan). *E. coli* ORN208, which has abnormal pili that is deficient in the adhesin sites of the normal pili of *E. coli* ORN178 was used as a control.

Early stationary phase cultures of *E. coli* ORN178 was harvested and washed twice with phosphate buffer saline (PBS). The bacterial suspension was mixed with an aqueous suspension of the nanoparticles for 5 min, and then the mixture was centrifuged at 6,000×g for 3 min. The supernatant containing free nanoparticles was removed, and the pellet was washed with PBS, centrifuged, and then re-suspended in PBS (1 mL). The sample for transmission electron microscopy (TEM) imaging was fixed in cacodylate buffered glutaraldehyde (3.5%, pH~7.2) at 4° C. for 12 h. A droplet of the sample was deposited on a carbon-coated copper grid, stained with uranyl acetate, and then dried in air for 30 min.

Early stationary phase cultures of *E. coli* ORN208 were prepared in an identical fashion as the *E. coli* ORN178 described above.

Figure 9:
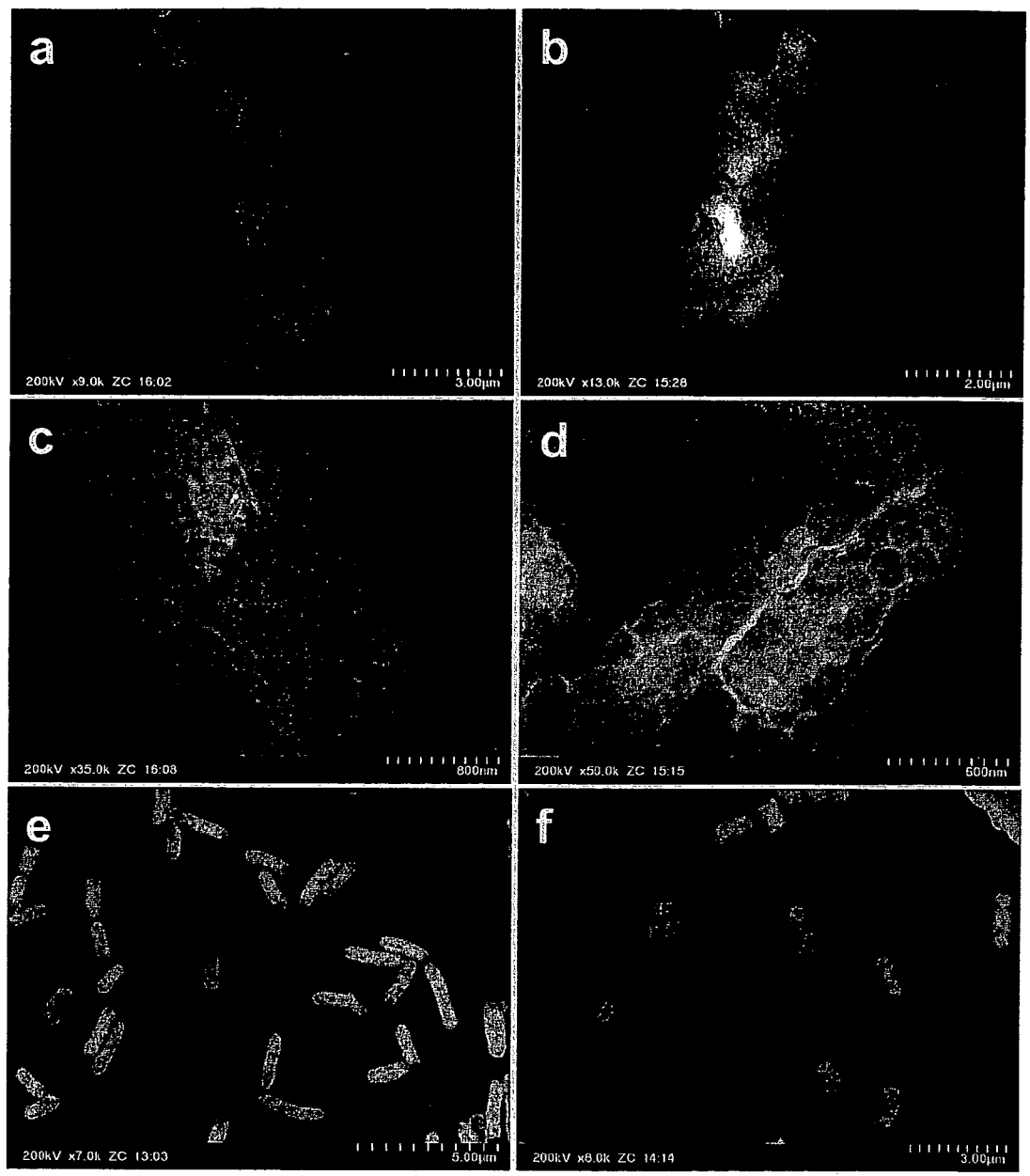
FIGS. 9a-d are TEM images of E. coli ORN178 agglutinated with D-mannose biofunctionalized nanoparticles.
FIG. 9e is a TEM image of E. coli ORN178 mixed with non-biofunctionalized nanoparticles.
FIG. 9f is a TEM image of adhesin deficient E. coli ORN208 mixed with biofunctionalized nanoparticles of the present invention.

FIG. 9 shows lower magnification of *E. coli* ORN178 after mixing with the D-mannose functional nanoparticles at 9*a* and 9*b*, and higher magnification of *E. coli* ORN178 after mixing with the D-mannose functional nanoparticles at 9*c* and 9*d*. The individual spheres visible in 9*c* and 9*d* are the individual biofunctionalized nanoparticles. As can be seen, there is significant agglomeration of the *E. coli* ORN178 cells with the nanoparticles. For comparison purposes, FIG. 9*e* shows a TEM image of the *E. coli* ORN178 mixed with the non-biofunctionalized nanoparticles 6A of FIG. 1. As can be seen, there is no agglomeration of the bacteria. Similarly, FIG. 9f shows the abnormal pili-containing E. coli ORN208 mediated with the D-mannose functional nanoparticles. However, as can be seen in the image, there is no agglomerated of the abnormal bacteria E. coli ORN208.

The cell-nanoparticle bindings were also confirmed to be irreversible, as was shown by subsequent incubation of the agglomerated E. coli ORN178 cells with a solution of free D-mannose molecules (10 mg/mL). Following incubation, there was no evidence of dissociation of the agglomerated complexes.

EXAMPLE 5

In this example, a Colony Forming Unit (CFU) Reduction Assay was used to evaluate the agglomeration of adhesin-specific biofunctionalized nanoparticles to E. coli.

Tryptic Soy Broth (TSB) and Tryptic Soy Agar (TSA) were used to cultivate E. coli strain ORN178.

Exponentially grown E. coli ($OD_{600}$=0.5) were diluted to $10^{-6}$, $10^{-7}$ and $10^{-8}$ with phosphate buffered saline (PBS) in duplicates. 250 μl of the diluted cultures were mixed with equal volume of mannose biofunctionalized nanoparticles, prepared as described above in Example 4, mannan biofunctionalized-nanoparticles, which were prepared in an equivalent protocol as that described for the mannose biofunctionalized nanoparticles, or PBS control. The mixtures were incubated at 37° C. for 15 minutes with gentle mixing every 5 minutes to allow agglomeration to occur. At the end of incubation, the whole content (500 μl) was transferred into a 100×15 mm Petri dish. 20 ml of sterile TSA, previously melted and equilibrated at 45° C., was then poured into the plate and allowed to be mixed with the culture and solidified. The plates were incubated at 37° C. for 24 hrs. At the end of incubation time, the number of colonies on the plates was enumerated.

Figure 10A:
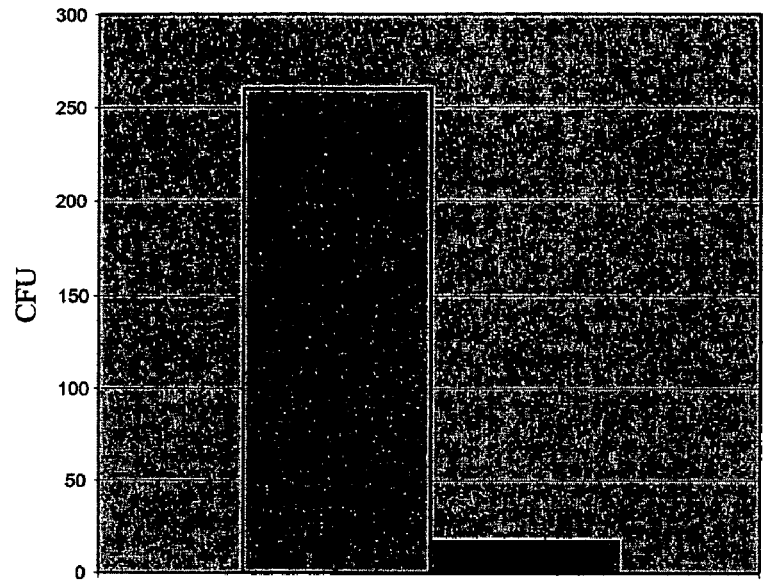
FIGS. 10A and 10B graphically compare the number of E. coli ORN178 colony forming units (CFU) obtained when mixed with biofunctionalized nanoparticles (right bar on the graph) and when mixed with a nonfunctionalized control substance (left bar on the graph).
Figure 10B:
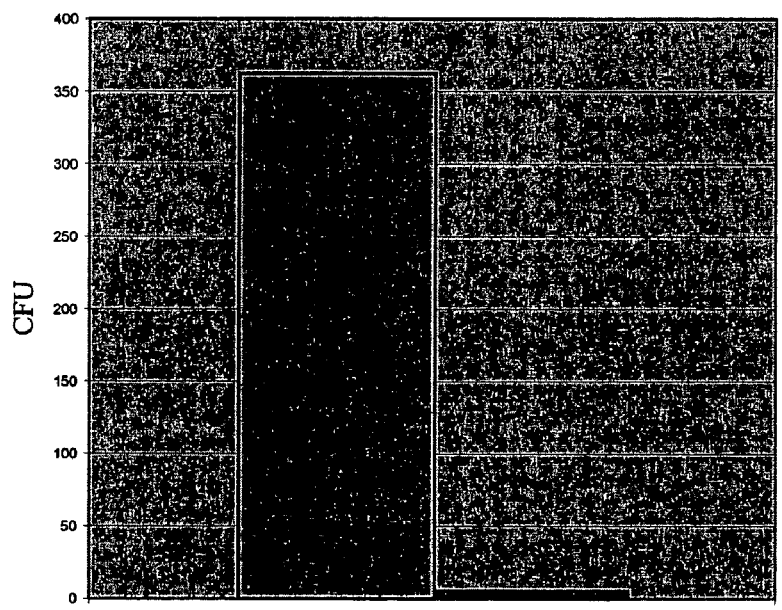

FIG. 10A shows approximately 260 CFU of the E. coli mixed with PBS (control), when no agglomeration of bacteria occurred compared to approximately 15 CFU obtained when the E. coli agglomerated with the mannose biofunctionalized nanoparticles ($10^{-7}$ dilution). Similarly, FIG. 10B shows approximately 360 CFU of the E. coli mixed with PBS (control), when no agglomeration occurred compared to approximately 5 CFU obtained when the E. coli agglomerated with the mannan biofunctionalized nanoparticles ($10^{-7}$ dilution).

The mannose biofunctionalized nanoparticles caused a 94% reduction in the number of colony forming units and mannan, which is a polymer of mannose, and will include more possible binding sites for the E. coli, caused a 99% reduction in the number of colony forming units.

EXAMPLE 6

The ability of the disclosed mannose biofunctionalized nanoparticles to achieve a marked reduction in C. jejuni CFU was compared to the CFU-reducing aggregation with a variety of other enteric bacteria. Strains of Escherichia coli, Salmonella typhi, Enterobacter aerogenes and Streptococcus faecalis were mixed with mannose biofunctionalized nanoparticles at nanoparticle:cell ratios of 0.3 to 3 μg:$10^6$ CFU. No significant reduction in CFU could be detected.

Table 2 is a comparison of colony forming units (CFU) obtained when 12.5 micrograms of mannose biifunctionalized nanoparticles (NP) per ml of nanoparticle mixture was combined with a variety of enteric bacteria: Campylobacter jejuni (CJ), Escherichia coli (EC) strain B, Salmonella typhimurium (ST), Enterobacter aerogenes (EA) and Streptococcus faecalis (SF).

TABLE 2

|  | CFU × $10^4$ | CFU × $10^5$ |
| --- | --- | --- |
| CJ control | 352-383* | 31-38 |
| CJ + NP | 146-199 | 7-15 |
| EC control | 397-426 | 40-48 |
| EC + NP | 393-430 | 46-47 |
| ST control | TNTC** | 283-298 |
| ST + NP | TNTC** | 278-303 |
| EA control | 326-393 | 27-38 |
| EA + NP | 317-323 | 32-42 |
| SF control | 320-380 | 30-41 |
| SF + NP | 367-394 | 33-41 |

*Ranges of duplicate platings
**Too numerous to count

The negative results with other enterics suggest that the aggregation of C. jejuni by mannose-bearing nanoparticles is not merely a non-specific binding. Commensal strains of E. coli bind mannose very weakly while pathogenic strains such as the E. coli ORN178 used in Examples 4 and 5, above, strongly bind both mannose and mannose oligosaccharides, so it is not surprising that the nanoparticles could not cause a reduction in E. coli CFU.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is identified that many embodiments may be conceived that do not achieve all of the advantages of some embodiments, yet the absence of a particular advantage shall not be construed to necessarily mean that such an embodiment is outside the scope of the present invention.

What is claimed is:

1. A process for agglomerating biologically active microorganisms comprising:
    contacting a first enteropathogenic microorganism with a first particle having an average diameter between about 30 nanometers and about 5 micrometers, the first particle comprising a polystyrene hydrophobic polymeric core and multiple polyethylene glycol hydrophilic polymeric linking agents bound to the polystyrene hydrophobic polymeric core, the polyethylene glycol hydrophilic linking agents having a degree of polymerization of between about 10 and about 200, the particle further comprising D-mannose bound to the hydrophilic linking agents, the D-mannose being bound to the hydrophilic linking agent at a distance from the hydrophobic core, the D-mannose comprising a first binding site for a first adhesin present on the surface of the enteropathogenic microorganism, wherein the enteropathic microorganism is E. coli or C. jejuni;
    binding the first adhesin of the first enteropathogenic microorganism to the first binding site of the D-mannose to form a particle/microorganism complex; and
    binding a second adhesin of a second enteropathogenic microorganism to a second binding site of the biofunctional material of the particle/microorganism complex, wherein the second enteropathogenic microorganism is *E. coli* or *C. jejuni* and thus agglomerating the first and second enteropathogenic microorganisms.

2. The process of claim 1, further comprising
contacting the particle/microorganism complex with a second particle, the second particle being structurally identical to the first particle; and
binding a third adhesin of the first enteropathogenic microorganism to a binding site of the second particle.

3. The process of claim 1, wherein the adhesin of the first enteropathogenic microorganism binds to the first binding site via an attachment/effacing binding mechanism.

4. The process of claim 1, wherein the first enteropathogenic microorganism and the second enteropathogenic microorganism are the same.

5. The process of claim 1, wherein the first enteropathogenic microorganism and the second enteropathogenic microorganism are different.

6. The process of claim 1, wherein the first binding site and the second binding site are structurally the same.

7. The process of claim 1, wherein the first binding site and the second binding site are structurally different.

8. The process of claim 1, further comprising releasing the first particle from an encapsulation in the area of the first enteropathogenic organism.

9. The process of claim 1, wherein the particle/microorganism complex is formed within the digestive system of an animal.

* * * * *